United States Patent
Jin et al.

(10) Patent No.: US 8,290,563 B2
(45) Date of Patent: Oct. 16, 2012

(54) ACTIVE DRY SENSOR MODULE FOR MEASUREMENT OF BIOELECTRICITY

(75) Inventors: Kyung-Soo Jin, Cheongju-si (KR); Jong-Jin Lim, Daejeon (KR); Jong-Gil Byeon, Chungbuk (KR); Eun-Tae Kim, Chungju-si (KR); Jin-Ho Park, Chungbuk (KR)

(73) Assignee: NeuroSky, Inc., San Jose, CA (US)

(*) Notice: Subject to any disclaimer, the term of this patent is extended or adjusted under 35 U.S.C. 154(b) by 896 days.

(21) Appl. No.: 10/585,500

(22) PCT Filed: Jun. 29, 2004

(86) PCT No.: PCT/KR2004/001573
§ 371 (c)(1),
(2), (4) Date: Feb. 17, 2009

(87) PCT Pub. No.: WO2005/065544
PCT Pub. Date: Jul. 21, 2005

(65) Prior Publication Data
US 2009/0156925 A1      Jun. 18, 2009

(30) Foreign Application Priority Data
Jan. 8, 2004    (KR) .................. 10-2004-0001127

(51) Int. Cl.
*A61B 5/04* (2006.01)
(52) U.S. Cl. ......... 600/383; 600/384; 600/393; 600/544
(58) Field of Classification Search .................. 600/372, 600/382–390, 395, 509, 544, 547; 330/85
See application file for complete search history.

(56) References Cited

U.S. PATENT DOCUMENTS

| | | | |
|---|---|---|---|
| 2,318,207 A | 5/1943 | Ellis | |
| 3,279,468 A | 10/1966 | LeVine | |
| 3,464,416 A | 9/1969 | Williams | |
| 3,508,541 A | 4/1970 | Westbrook et al. | |
| 3,669,119 A | 6/1972 | Symmes | |
| 4,202,354 A * | 5/1980 | Smith et al. | 600/544 |
| 4,535,779 A * | 8/1985 | Ober | 600/384 |
| 4,608,987 A | 9/1986 | Mills | |

(Continued)

FOREIGN PATENT DOCUMENTS
CN         1745702 A      3/2006
(Continued)

OTHER PUBLICATIONS

PCT/US07/024662, International Search Report & Written Opinion, Apr. 24, 2008.

(Continued)

*Primary Examiner* — Linda Dvorak
*Assistant Examiner* — Brian M Antiskay
(74) *Attorney, Agent, or Firm* — Van Pelt, Yi & James LLP

(57) ABSTRACT

An active dry sensor module for measurement of bioelectricity is disclosed. The active dry sensor module of the present invention excludes the use of a conductive gel, thereby not supplying unpleasantness and discomfort to a reagent and preventing the interference of the signal due to a noise component. Further, the active dry sensor module of the present invention amplifies the biomedical signal to a desired level, thereby precisely and easily measuring the biomedical signal.

8 Claims, 7 Drawing Sheets

U.S. PATENT DOCUMENTS

| | | | |
|---|---|---|---|
| 4,610,259 A | 9/1986 | Cohen et al. | |
| 4,646,747 A * | 3/1987 | Lundback | 600/387 |
| 4,709,702 A * | 12/1987 | Sherwin | 600/383 |
| 4,781,196 A | 11/1988 | Killion | |
| 4,833,422 A * | 5/1989 | Atwell | 330/254 |
| 4,867,166 A | 9/1989 | Axelgaard et al. | |
| 4,949,726 A | 8/1990 | Hartzell et al. | |
| 4,955,388 A | 9/1990 | Silberstein | |
| 4,967,038 A | 10/1990 | Gevins et al. | |
| 5,038,782 A | 8/1991 | Gevins et al. | |
| 5,169,380 A | 12/1992 | Brennan | |
| 5,305,746 A | 4/1994 | Fendrock et al. | |
| 5,339,826 A | 8/1994 | Schmidt et al. | |
| 5,800,351 A | 9/1998 | Mann | |
| 5,983,129 A | 11/1999 | Cowan et al. | |
| 6,001,065 A | 12/1999 | DeVito | |
| 6,047,202 A | 4/2000 | Finneran et al. | |
| 6,080,110 A | 6/2000 | Thorgersen | |
| 6,154,669 A | 11/2000 | Hunter et al. | |
| 6,181,974 B1 | 1/2001 | Springer, Jr. | |
| 6,254,536 B1 | 7/2001 | DeVito | |
| 6,272,378 B1 | 8/2001 | Baumgart-Schmitt | |
| 6,296,543 B1 | 10/2001 | Andrews | |
| 6,353,396 B1 | 3/2002 | Atlas | |
| 6,381,481 B1 | 4/2002 | Levendowski et al. | |
| 6,445,940 B1 | 9/2002 | Gevins et al. | |
| 6,574,513 B1 | 6/2003 | Collura et al. | |
| 6,609,017 B1 | 8/2003 | Shenoy et al. | |
| 6,636,763 B1 | 10/2003 | Junker et al. | |
| 6,731,964 B2 | 5/2004 | Shenoy et al. | |
| 6,993,380 B1 | 1/2006 | Modarres | |
| 7,058,445 B2 | 6/2006 | Kemere et al. | |
| 7,127,283 B2 | 10/2006 | Kageyama | |
| 7,460,903 B2 | 12/2008 | Pineda et al. | |
| 7,546,158 B2 | 6/2009 | Allison et al. | |
| 7,551,952 B2 | 6/2009 | Gevins et al. | |
| 2001/0044573 A1 | 11/2001 | Manoli et al. | |
| 2001/0056225 A1 | 12/2001 | DeVito | |
| 2002/0091335 A1 | 7/2002 | John et al. | |
| 2004/0073129 A1 | 4/2004 | Caldwell et al. | |
| 2004/0097824 A1 | 5/2004 | Kageyama | |
| 2004/0122303 A1 | 6/2004 | Kopke | |
| 2004/0138578 A1 | 7/2004 | Pineda et al. | |
| 2004/0193068 A1 | 9/2004 | Burton et al. | |
| 2004/0267152 A1 | 12/2004 | Pineda | |
| 2005/0278009 A1 | 12/2005 | Bona et al. | |
| 2007/0066914 A1 | 3/2007 | Le et al. | |
| 2007/0093706 A1 | 4/2007 | Gevins et al. | |
| 2007/0106169 A1 | 5/2007 | Fadem | |
| 2007/0106170 A1 | 5/2007 | Dunseath et al. | |
| 2007/0112277 A1 | 5/2007 | Fischer et al. | |
| 2007/0151106 A1 | 7/2007 | Steunenberg et al. | |
| 2007/0173733 A1 | 7/2007 | Le et al. | |
| 2007/0207858 A1 | 9/2007 | Breving | |
| 2007/0225585 A1 | 9/2007 | Washbon et al. | |
| 2007/0238945 A1 | 10/2007 | Delic et al. | |
| 2007/0249952 A1 | 10/2007 | Rubin et al. | |
| 2008/0004512 A1 * | 1/2008 | Funderburk et al. | 600/309 |
| 2008/0177197 A1 | 7/2008 | Lee et al. | |
| 2008/0281392 A1 | 11/2008 | Paolizzi et al. | |

FOREIGN PATENT DOCUMENTS

| | | |
|---|---|---|
| DE | 3025955 | 1/1982 |
| DE | 4228351 | 4/1994 |
| DE | 10153360 | 5/2003 |
| EP | 1264575 | 12/2002 |
| JP | H07-27505 U | 5/1995 |
| JP | 2002095637 | 4/2002 |
| JP | P2002-177231 | 6/2002 |
| KR | 20010045348 | 6/2001 |
| WO | 9714357 | 4/1997 |
| WO | 0045701 | 8/2000 |
| WO | 0056211 | 9/2000 |
| WO | 2002/100267 | 12/2002 |
| WO | WO 2005/065544 | 7/2005 |
| WO | 2007109745 | 9/2007 |

OTHER PUBLICATIONS

Vanrijn et al., Low-Cost Active Electrode Improves the Resolution in Biopotential Recordings, IEEE Engineering in Medicine and Biology Society, 1996 18th Annual International Conference, pp. 101-102.

Makeig et al., Changes in Alertness are a Principal Component of Variance in the EEG Spectrum, NeuroReport 1995.

Makeig et al., Independent Component Analysis of Electroencephalographic Data, Advances in Neural Information Processing Systems, pp. 145-151, 1996.

Ungureanu et al., Independent Component Analysis Applied in Biomedical Signal Processing, Measurement Science Review, vol. 4, Section 2, 2004.

Benca et al., EEG Alpha Power and Alpha Power Asymmetry in Sleep and Wakefulness, pp. 430-436, 1999.

John T.Cacioppo, Feelings and Emotions: Roles for Electrophysiological Markers, pp. 234-243, 2004.

Ranganath et al., Frontal EEG Alpha Asymmetry, Depression, and Cognitive Functioning, pp. 449-478, 1998.

Hebert et al., Physiological Stress Response to Video-Game Playing: The Contribution of Built-In Music, pp. 2371-2380, 2005.

Annika S. Smit, Mental Effort Affects Vigilance Enduringly: After-Effects in EEG and Behavior, pp. 239-243, Apr. 21, 2004.

Wolpaw et al., Brain-Computer Interfaces for Communication and Control, pp. 767-791, 2002.

Kaplan et al., Application of the Change-Point Analysis to the Investigation of the Brains's Electrical Activity, Chapter 7 in Brodsky et al., Nonparametric Statistical Diagnosis: Problems and Methods, pp. 333-388, 2000.

Kaplan et al., Probability Patterns of the Human EEG Narrow-Band Differential Spectra During Memory Processes, Jan. 20, 1997.

Fingelkurts et al., The Regularities of the Discrete Nature of Multi-Variability of EEG Spectral Patterns, Apr. 26, 2001.

Shishkin et al., Combining the Extremities on the Basis of Separation: A New Approach to EEG/ERP Source Localization, Nov. 2004.

Kaplan et al., Macrostructural EEG Characterization Bases on NonParametric Change Point Segmentation: Application to Sleep Analysis, Jan. 8, 2001.

Kaplan et al., Unconscious Operant Conditioning in the Paradigm of Brain-Computer Interface Based on Color Perception, Jun. 29, 2004.

Levichkina et al., Unconscious Context Control of Visual Perception of Simple Stimuli: A Study Using Evoked Potentials, Aug. 2, 2007.

Landa et al., A Model for the Speed of Memory Retieval, Published Oct. 21, 2003.

Kaplan et al., Nonstationary Nature of the Brain Activity as Revealed by EEG/MEG: Methodological, Practical and Conceptual Challenges, Jul. 28, 2005.

A. Kaplan, The Problem of Segmental Description of Human Electoencephalogram, Mar. 18, 1998.

Borisov et al., Analysis of EEG Structural Synchrony in Adolescents with Schizophrenic Disorders, Jun. 7, 2004.

Coan et al., Frontal EEG Asymmetry as a Moderator and Mediator of Emotion, pp. 7-49, 2004.

* cited by examiner

ACTIVE DRY SENSOR MODULE FOR MEASUREMENT OF BIOELECTRICITY

This application claims priority, under 35 USC §119, from Korean Patent Application No. 10-2004-0001127 filed on Jan. 8, 2004 in the Korean Intellectual Property Office, the disclosure of which is incorporated herein in its entirety by reference.

FIELD OF THE INVENTION

The present invention relates to a sensor module for measurement of bioelectricity, which improves a general flat-type passive electrode, and more particularly to an active dry sensor module for measurement of bioelectricity, which filters the bioelectricity plural times at a rated capacity and shields interference and noise components due to a power line so as to increase reliability of the bioelectricity, and omits the use of a conductive gel so as to suppress discomfort supplied to a reagent.

BACKGROUND OF THE INVENTION

Bioelectricity, which refers to an ultra-fine biomedical signal flowing through the human body, is a signal of the shape of current or voltage generated from a nerve cell or a muscular cell. The bioelectricity is classified into ElectroCardioGram (ECG), ElectroMyoGram (EMG), ElectroOculoGram (EOG), ElectroEncephaloGram (EEG), and so forth. The source of the bioelectricity is a membrane potential, which is stimulated to produce an action potential under predetermined conditions. The measurement of the action potential in a single cell is achieved by a special fine electrode, and this action potential is the source of a bioelectric potential.

The measurement of the action potential in a larger unit is achieved by a surface electrode. In this case, an electric field generated due to the action of many cells distributed around the electrode is measured. Electrical conduction in a living matter is achieved by ions, but electrical conduction in a measurement system is achieved by electrons, thereby requiring an electrode.

Among biomedical signals, particularly, variation in a potential of a brain wave signal generated from the scalp of a human body is approximately 10~100 µV. The biomedical signal having above size is weak so that this signal cannot be detected by the human body. However, the biomedical signal, which is abnormal, is bad for health of the human body, such as the lowering of the function of the human body and the generation of disease, and is dangerous. Thus, it is important to maintain the normal state of the biomedical signal. Further, biomedical signals are used as data for clinical diagnosis in the medical field. For example, biomedical signals are sources for diagnosing a reagent's illness by means of a non-invasive method, and are essential in clinical examination.

When the above biomedical signal is measured, an electrode of a sensor module is attached to the skin of the human body. The electrode, which is attached to the skin, is the most essential element of the sensor module. Generally, in order to sense an electric signal, the electrode is made of a conductor, through which current flows. Further, in order to improve conductibility, the electrode is made of conductive material made of gold (Au) or silver (Ag).

FIGS. 9A and 9B are perspective and sectional views of a conventional electrode for measurement of bioelectricity. The conventional electrode for measurement of bioelectricity is made of metal and has a disk shape. That is, the conventional electrode for measurement of bioelectricity comprises a base 3 formed in the shape of a foam pad, a fabric, a nonwoven fabric, or a tape including synthetic polymer and natural polymer, and provided with an acryl-grouped biocompatible adhesion paste deposited on one surface thereof; a stiffener 2 made of polymer and attached to the other surface of the case 3 for preventing evaporation of moisture; a snap 1 made of brass and installed at the central portion of the stiffener 2, and an electrode element 4 made of plastic reinforced with glass fiber and deposited with silver/silver chloride, the snap 1 and the electrode element 4 being fixed to each other; a conductive hydro gel adhesive agent 5 coating the exposed surface of the electrode element 4; and a release film 6 attached to the hydro gel adhesive agent 5 and the remaining adhesion paste on the base 3 for protecting the hydro gel adhesive agent 5 and the remaining adhesion paste on the base 3.

The above conventional electrode for measurement of bioelectricity uses a conductive adhesion gel for attaching an electrode element, such as the scalp electrode, to the skin. In the case that the conventional electrode uses the conductive adhesion gel, a long preparation time is required. Further, the conductive adhesion gel supplies unpleasantness or discomfort to a reagent due to its own viscosity. In order to obtain more precise measurement results, before the conductive adhesion gel is applied to the scalp of the regent, the scalp is slightly rubbed. Such an action generates damage to the scalp, thus being not preferable. It is a well-known fact by the research of brain that the damage to the scalp increases the danger of infection of a virus transmitted through blood, such as Human Immunodeficiency Virus (HIV), Hepatitis C Virus (HCV), or Creutzfeldt-Jacob Disease (CJD).

The biomedical signal measured by the electrode element is applied to an electronic circuit for processing the signal through a wire (not shown) having a length of several meters. Here, in the case that the biomedical signal to be measured is EEG, the level of the signal is excessively fine, i.e., several tens of µV. Accordingly, when the wire is not shielded, there is an ample probability of that the discrimination of the signal is rapidly deteriorated due to a noise component such as interference of power of 60 Hz. That is, a biomedical signal having a fine level is transmitted to an amplification circuit through the wire having a comparatively long length so that the biomedical signal is amplified by the amplification circuit. Here, the biomedical signal may be attenuated by the wire. Further, in the case that the biomedical signal is interfered by external noise, the amplification circuit amplifies the external noise as well as the biomedical signal. Although an electronic circuit, such as a high or low band-pass filter, is prepared to filter the signal, the noise components, which were already introduced into the signal during the signal transmission, are not completely eliminated and are measured/analyzed together with the biomedical signal.

In order to solve the above problems, many methods have been proposed. In one method, the interference due to noise of 60 Hz is reduced through a shielded wire. However, the above method still has drawbacks, such as loss of the signal due to the length of the wire and interference by a magnetic phenomenon due to a loop of the long wire, thus being disadvantageous in terms of noise characteristics, reliability in measurement, or costs.

SUMMARY OF THE INVENTION

An active dry sensor module for measurement of bioelectricity is provided that prevents the interference of noise components, amplifies a biomedical signal to a treatable level to precisely and easily measure the biomedical signal, and omits the use of a conductive gel to suppress the generation of reagent's unpleasantness or discomfort.

In accordance with an aspect of the present invention, an active dry sensor module is provided that comprises a hollow main body provided with an insertion hole formed through the upper surface thereof; a cap interlocked with the insertion hole, and provided with a uniform central internal cross section and an upper fringe protruded from the upper surface thereof; an active electrode inserted into the cap so that the active electrode is slidable, and provided with the upper surface exposed to the outside and a latching protrusion protruded from the lower part thereof and latched onto a lower end of the cap; a spring provided with one end contacting the lower part of the active electrode, installed in the main body, and electrically connected to the main body; and an amplification circuit installed in the main body, under the condition that the amplification circuit contacts the other end of the spring, for receiving and processing a biomedical signal passed through the spring.

Preferably, the active dry sensor module may further comprise a holder fixedly inserted into the through hole, and the cap may be inserted into the holder. Further, preferably, a headset may be inserted between the cap and the holder so that the main body is attached to and detached from the headset. The amplification circuit includes an instrumentation amplifier for amplifying the biomedical signal and adjusting a common mode rejection ratio and a pass band; a band-pass filter for filtering the biomedical signal passed through the instrumentation amplifier; and a notch filter for eliminating a noise component contained in the biomedical signal. Preferably, the active electrode and the spring may be plated with gold or silver. Further, preferably, the active electrode may have a curved surface contacting a skin. Alternately, preferably, the active electrode may have an uneven surface contacting a skin.

The active dry sensor module for measurement of bioelectricity in accordance with the present invention excludes the use of a conductive gel, thereby not supplying unpleasantness and discomfort to a reagent and preventing the danger of viral infection. Further, the active dry sensor module of the present invention excludes the use of a wire for transmission of a biomedical signal, thereby preventing the interference of the signal due to a noise component generated from a power source. Moreover, the active dry sensor module of the present invention amplifies the biomedical signal to a designated treatable level, thereby precisely and easily measuring the biomedical signal.

DETAILED DESCRIPTION OF A PREFERRED EMBODIMENT

Figure 1A:
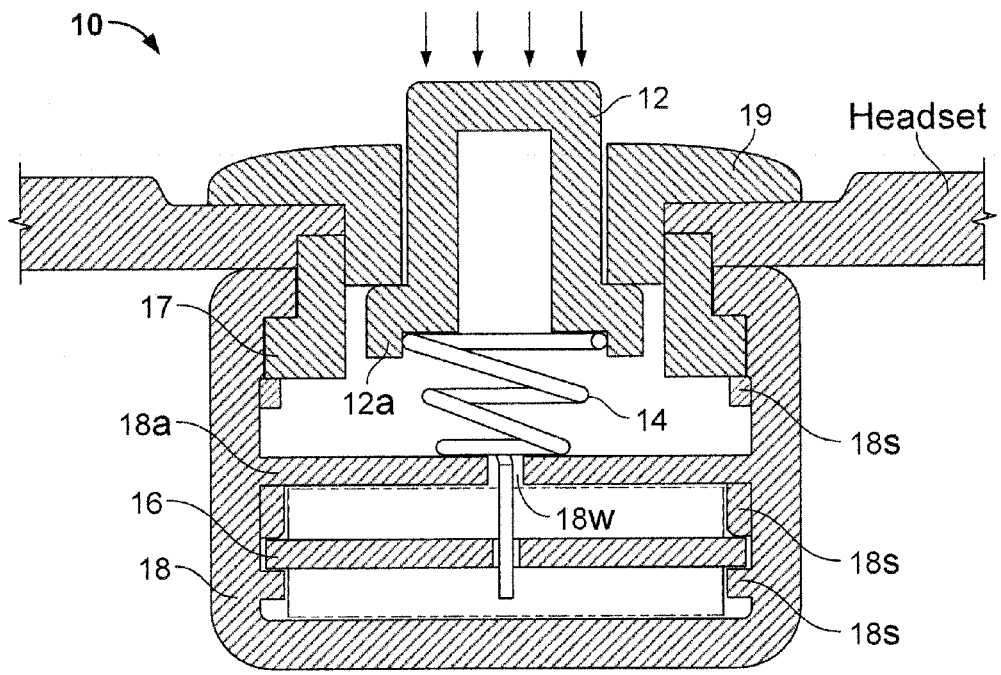
FIGS. 1A and 1B illustrate partial sectional views showing the operation of an active dry sensor module for measurement of bioelectricity in accordance with the present invention.
Figure 1B:
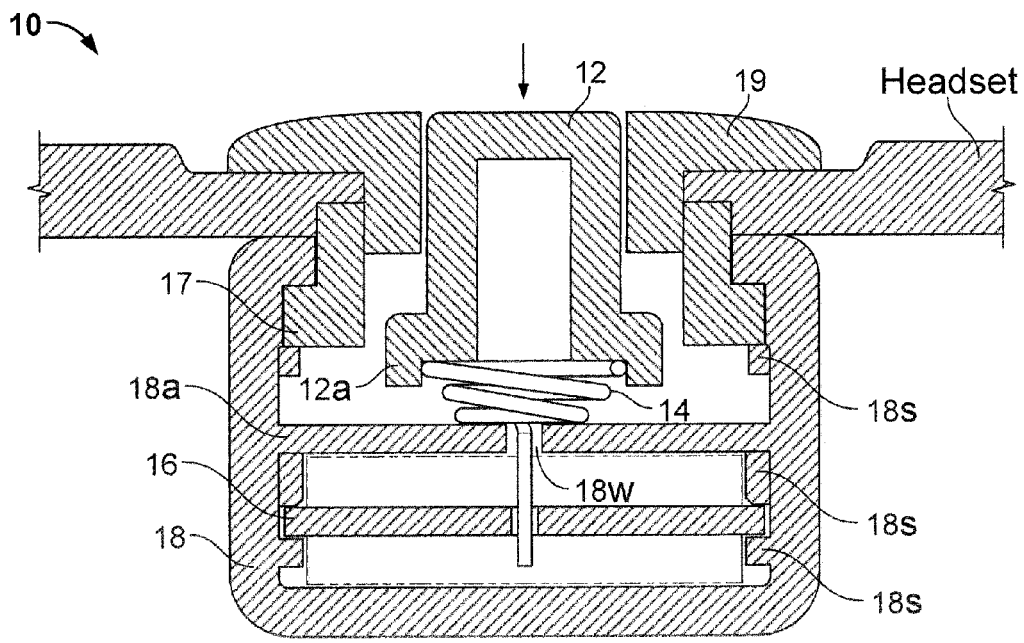

Now, a preferred embodiment of the present invention will be described in detail with reference to the accompanying drawings. The accompanying drawings have been made only for a better understanding of the embodiment of the present invention. Thus, the accompanying drawings and the description with reference to the drawings do not limit the scope and spirit of the invention. In the drawings, the same or similar elements are denoted by the same reference numerals even through they are depicted in different drawings.

Figure 2:
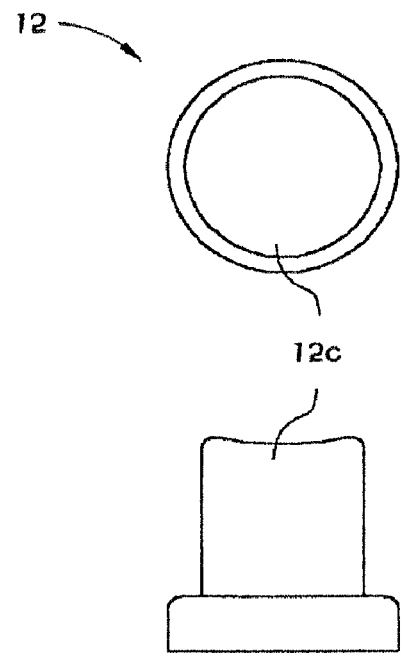
FIG. 2 illustrates plan and side views of a concave active electrode of the sensor module of the present invention.
Figure 3:
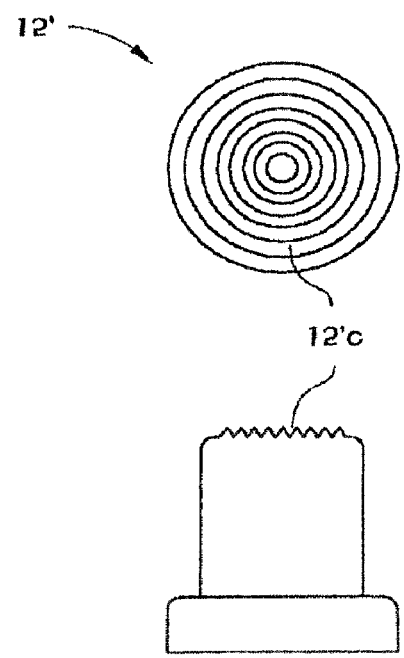
FIG. 3 illustrates plan and side views of a toothed active electrode of the sensor module of the present invention.

An active dry sensor module 10 for measurement of bioelectricity in accordance with the present invention comprises an active electrode 12, a resilient member 14, such as a spring, an amplification circuit 16, a main body 18, and a holder 17 and a cap 19 necessary for fixing the sensor module 10 when the sensor module 10 is installed at a headset. The active electrode 12 is interlocked with the cap 19, and vertically slides relative to the cap. The upper part of the active electrode 12 is exposed to the outside to contact skin of a user. The active electrode also has a latching protrusion 12a, which is latched to the cap 19 inserted into the main body 18, is protruded from the lower part of the active electrode 12 located in the main body 18. The active electrode 12 is the element directly contacting the scalp when the active electrode 12 measures a biomedical signal, for example, EEG. Accordingly, since the reliability of the measured value of the biomedical signal depends on the active electrode 12, preferably, the active electrode 12 is plated with gold or silver so that the conductibility of the active electrode 12 is improved and current easily flows through the active electrode 12. As shown in FIGS. 2 and 3, preferably, the surface of the active electrode 12 contacting the scalp of the reagent is concave or toothed so that the contact surface of the active electrode 12 stably contacts the scalp of the reagent for a long time. The concave active electrode 12 directly contacts a bare portion of the scalp, and the toothed active electrode 12' contacts a portion having hair of the scalp. Preferably, the concave active electrode 12 is configured such that a contact surface 12c of the concave active electrode 12 is similar to the curved surface of the scalp. Further, preferably, the toothed active electrode 12' is configured such that a plurality of circular protuberances 12'c are formed on the contact surface of the toothed active electrode 12', and contacts the portion having hair of the scalp.

Hereinafter, although this embodiment describes a concave active electrode 12 (FIG. 2), the toothed active electrode 12' (FIG. 3) may also be used. Thus, the invention is not limited to any particular shape and/or material of the active electrode.

In order to attach the conventional electrode for measurement of bioelectricity to the scalp, a conductive gel containing a Cl⁻ component is applied to the scalp, and then the electrode is attached thereto. However, when the conductive gel is used, positive (+) ions of metal flowing from the electrode and negative (−) ions on the surface of the electrode attract each other, thereby forming an electrical double layer, thus generating polarization between the electrode and the gel. Accordingly, a half cell potential, which is an undesired potential difference, is generated between the electrode and a measured portion. The above half cell potential is several hundreds mV, and more particularly, in the case that the electrode is a generally used Ag—AgCl electrode, the half cell potential is approximately 220 mV. Generally, the half cell potential is removed by common mode voltage of an instrumentation amplifier (IA), which will be later connected to the electrode, and only a brain wave signal serving as a differential component is amplified and is then outputted.

The quality of the brain wave component, passed through the IA, depends on an electrical resistance component of an interface between the skin and a contact surface of an electrolyte. The intensity of the resistance component reaches several tens of kΩ~several hundreds of kΩ according to a variable, such as the state of the skin, the concentration of the gel used in the electrode, or the required time after the gel is applied to the skin. Accordingly, in order to obtain low impedance having reliable stability in an initial stage, an electrode gel containing NaCl having a high concentration of 5~10% is applied to the skin, such as the scalp from which a horny layer is removed. Consequently, this minimizes a DC offset voltage, generated from a route from the skin to the surface of the electrode, and the resistance component, and means that a proper electrode is selected and the state of the skin, to which the electrode is attached, is satisfactory. In the mechanical design of the electrode, the electrode must be designed such that an artifact due to a movement between the skin and an electrolyte and a movement between the electrolyte and a bonding portion of the electrode is not generated in consideration of the shape of the scalp, to which the electrode is attached.

When the above conventional scalp electrode is used, it takes a long time to prepare the scalp electrode. For example, since the time taken to apply one conventional electrode to the scalp is 20 seconds to 30 seconds, the time taken to measure 64 channels is approximately 30 minutes. In order to shorten the above time, the electrode may have a cap shape. However, in this case, it also takes a considerable time to prepare the electrode. Further, when the conductive gel is used, the conductive gel supplies unpleasantness and discomfort to a reagent except for clinical testing, and damages the scalp in order to perform precise measurement as described above, thereby causing the danger of viral infection.

Accordingly, in order to solve the disadvantages of the conventional electrode for measurement of electricity, the active dry sensor module 10 for measurement of bioelectricity in accordance with the present invention employs the active electrode 12 for suppressing the half cell potential and the generation of noise without the conductive gel.

A biomedical signal induced from the active electrode 12 is transmitted to the amplification circuit 16 through the resilient member 14 plated with the same material as that of the active electrode 12.

Figure 4:
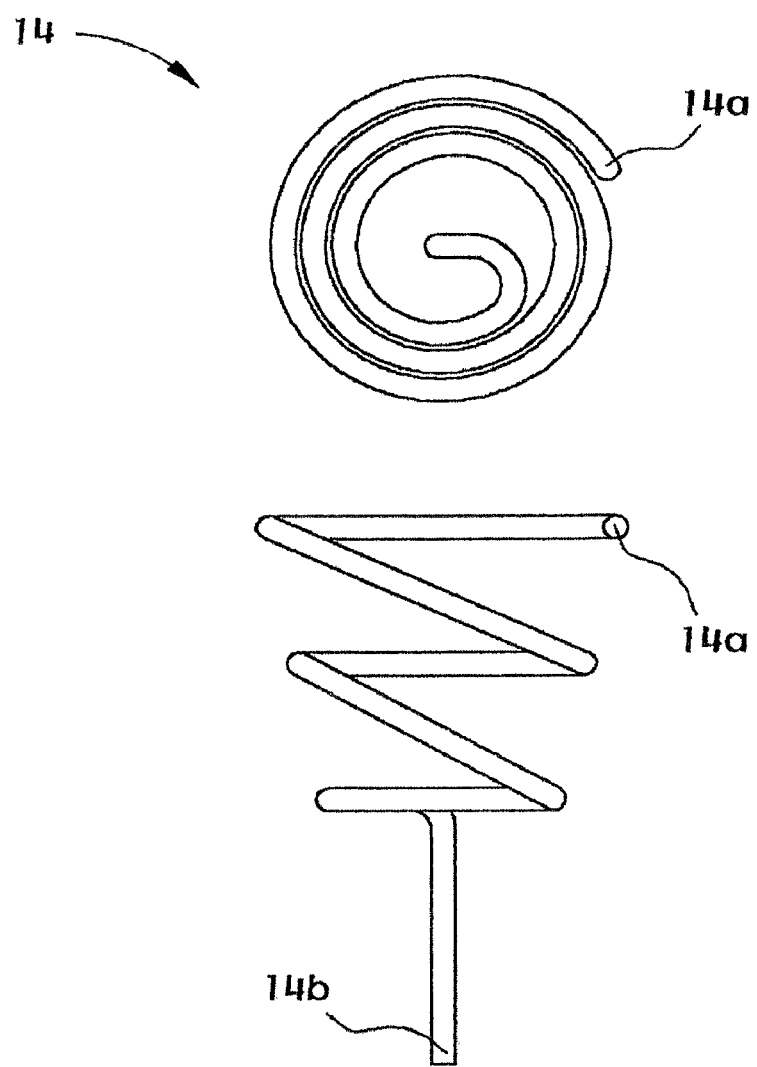
FIG. 4 illustrates plan and side views of a spring of the sensor module of the present invention.

FIG. 4 illustrates plan and side views of the spring of the sensor module of the present invention. The resilient member 14 (which may be a spring), is installed in the main body 18, substitutes for the wire having a considerable length installed in the conventional sensor module. Preferably, the spring 14 is a compressed spring, which repels against the compressive force. Further, preferably, in the same manner as the active electrode 12, the spring 14 is plated with gold or silver so as to transmit the biomedical signal transmitted through the active electrode 12 to the amplification circuit 16. One end 14a of the spring 14 mechanically contacts the lower part of the active electrode 12 and receives the biomedical signal, and the received biomedical signal is transmitted to the amplification circuit 16 connected to the other protruded end 14b of the spring 14 by soldering.

The spring 14 of the sensor module 10 of the present invention serves as pressure supply means for applying the active electrode 12 to the scalp without the conductive gel, and serves to damp pressure generated when the active electrode 12 contacts the scalp. Further, the spring 14 applies pressure of a proper intensity to the active electrode 12, thereby preventing the pressure on the interface between the scalp and the active electrode 12 from causing reagent's discomfort and a mark of the active electrode 12 from remaining on the interface after the measurement.

Figure 5:
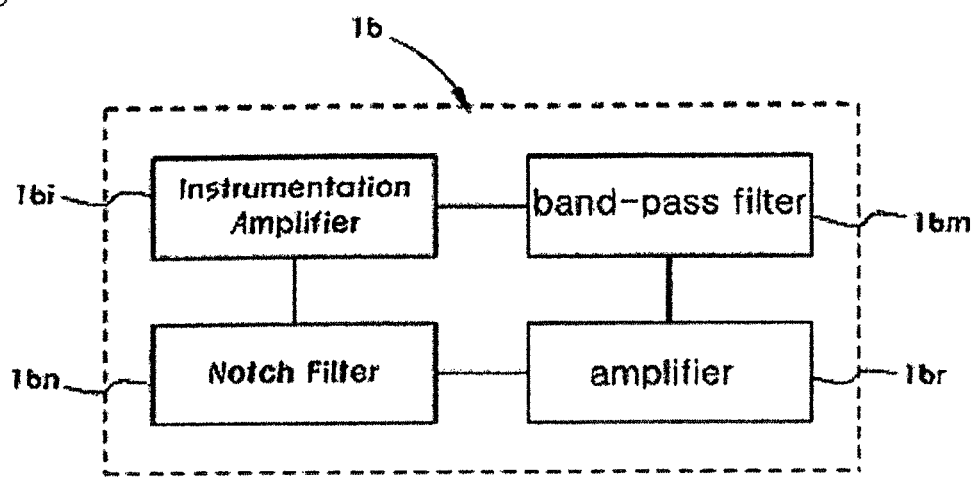
FIG. 5 is a block diagram illustrating the constitution of an amplification circuit of the sensor module of the present invention.

FIG. 5 is a block diagram illustrating the constitution of the amplification circuit of the sensor module of the present invention. As shown in FIG. 5, the amplification circuit 16 includes an instrumentation amplifier (IA) 16$i$, a notch filter 16$n$, a band-pass filter 16$m$, and an amplifier 16$r$. The protruded end 14$b$ of the spring 14 is connected to the amplification circuit 16 by soldering so that the protruded end 14$b$ is fixed to the lower portion of the inside of the main body 18. The amplification circuit 16 receives the biomedical signal passed through the spring 14, and amplifies and filters the biomedical signal so that the biomedical signal is easily measured and formed.

The IA, which is conventionally used for measurement of bioelectricity, is a differential amplifier including a buffer amplifier for eliminating the half cell potential and picking out only a pure biomedical signal. The most important parameter of the IA is a common mode rejection ratio (CMRR). The CMRR is a parameter indicating how many signals existing by simultaneous input are removed, and is obtained by dividing a common gain value by a differential gain value. The higher the CMRR is, the better characteristics the differential amplifier indicates. When the conventional Ag/AgCl electrode is used, an impedance component between the electrode and the scalp is approximately 10~30 kΩ. The IA used for preventing disturbance of an input signal due to the impedance of the electrode and processing the biomedical signal must have an input impedance of more than 100 kΩ, a CMRR of more than 80 dB, and an overall gain of approximately 1,000~100,000 times.

The active electrode 12 of the sensor module 10 of the present invention is a dry electrode, which does not use an electrolyte. Since the input impedance of the active electrode 12 is increased maximally to hundreds kΩ (200 kΩ~300 kΩ), the conventional IA cannot be applied to the active electrode 12. Accordingly, in order to reduce the influence of the increased input impedance of the sensor module 10 and an input noise component thereby, the IA 16$i$ has an input impedance of $10^{13}$ kΩ, a CMRR of more than 120 dB, and band pass characteristics, which has a signal pass band of 0.1~40 Hz. The above characteristics cannot be exhibited by the conventional IA, but are caused by a specially created circuit. That is, the IA includes three amplifiers so that one amplifier serves as a differential amplifier and the remaining two amplifiers form a feedback loop, thereby having band pass characteristics as well as an amplification function. Here, the amplification degree of the IA is increased to several ten thousand times by varying the value of an internal element, and the amplifier 16$r$ serving as the differential amplifier does not amplify a common mode signal for identically driving two input values, thereby not exhibiting an interference voltage to the output.

The noise component is additionally eliminated by the band-pass filter 16$m$. However, since the noise component of 60 Hz is generated from a power source as well as a human body, the notch filter 16$n$ for additionally eliminating the noise component of 60 Hz is provided. The notch filter 16$n$ eliminates the noise component of 60 Hz, and filters the biomedical signal processed by the IA 16i one more time, thus adjusting a frequency band. Accordingly, the notch filter 16n serves as an additional amplifier.

Figure 6:
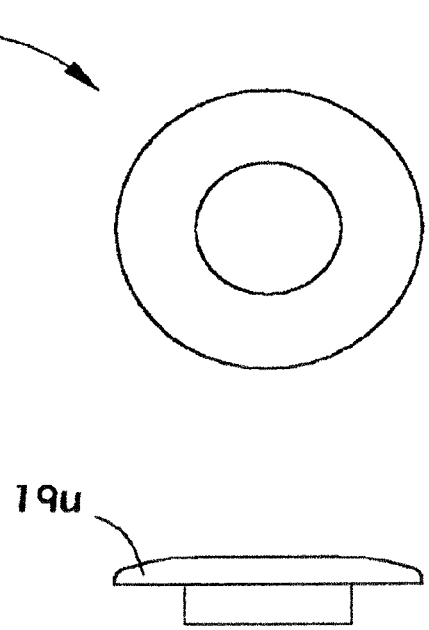
FIG. 6 illustrates plan and side views of a cap of the sensor module of the present invention.
Figure 7:
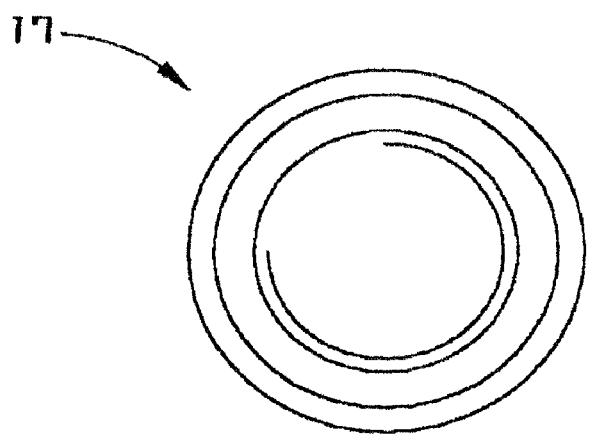
FIG. 7 illustrates plan and side views of a holder of the sensor module of the present invention.
Figure 7:
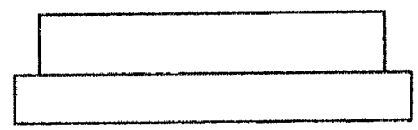

FIG. 6 illustrates plan and side views of a cap of the sensor module of the present invention, and FIG. 7 illustrates plan and side views of a holder of the sensor module of the present invention. An insertion hole 18h, into which the holder 17 and the cap 19 are inserted, is formed through the upper surface of the main body 18, and the active electrode 12, the spring 14, and the amplification circuit 16 are located at the inside and outside of the main body 18. The holder 17 is fixedly inserted into the insertion hole 18h, and screw threads and screw hollows, which are engaged with each other, are respectively formed at the upper part of the holder 17 and the lower part of the cap 19 so that the cap 19 is rotated and fixed to the holder 17. In this case, the holder 17 is integrated with the main body 18, and then the integrated assembly of the holder 17 and the main body 18 is molded.

The cap 19 is used when the sensor module 10 is fixed to a headset. When the cap 19 is rotated, the height of the cap 19 is changed so as to firmly fix the module 10 to the headset. That is, the sensor module 10 of the present invention is simply and firmly attached to and detached from the headset by rotating the cap 19. Preferably, the cross section of the central part of the cap 19 has a regular ring shape such that an upper protrusion 19u of the cap 19 is protruded outwardly.

In order to eliminate the signal interference due to the influence of external environment, preferably, the main body 18 is made of insulating material, such as synthetic resin without conductance, and has an external cross section of a rectangular shape and an internal cross section of a circular shape so that the main body 18 has a hollow structure.

Figure 8:
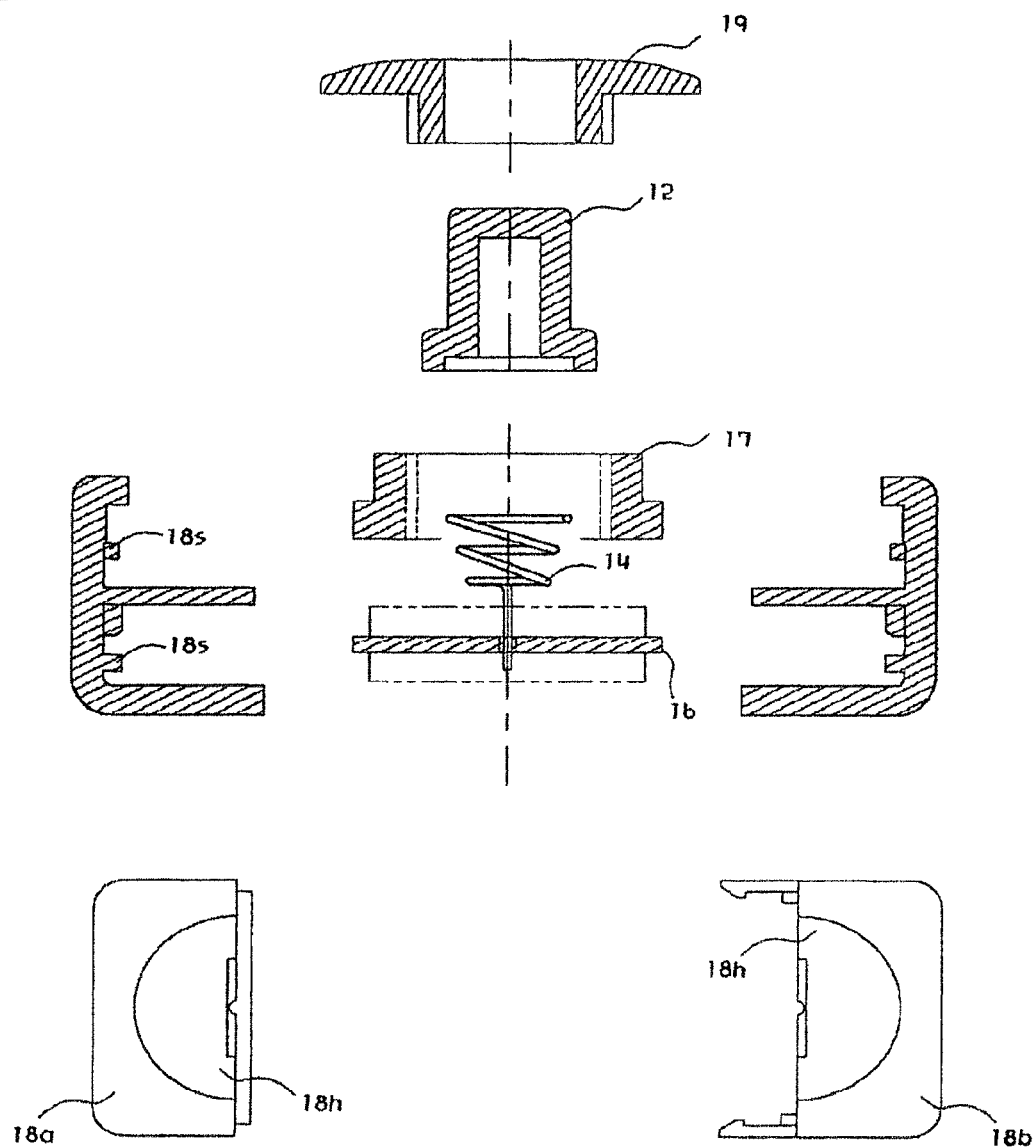
FIG. 8 is an exemplary view showing the sensor module of the present 5 invention in an assembled state.
Figure 9A:
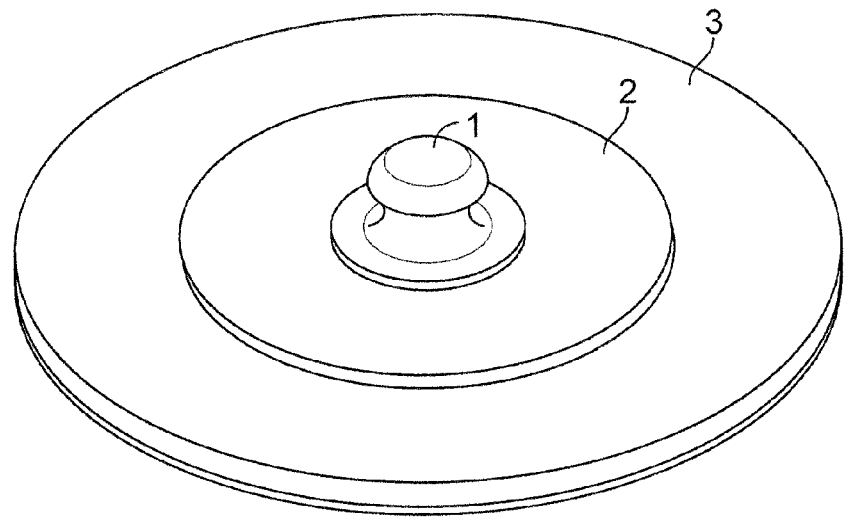
FIGS. 9A and 9B are perspective and sectional views of a conventional electrode for measurement of bioelectricity.
Figure 9B:
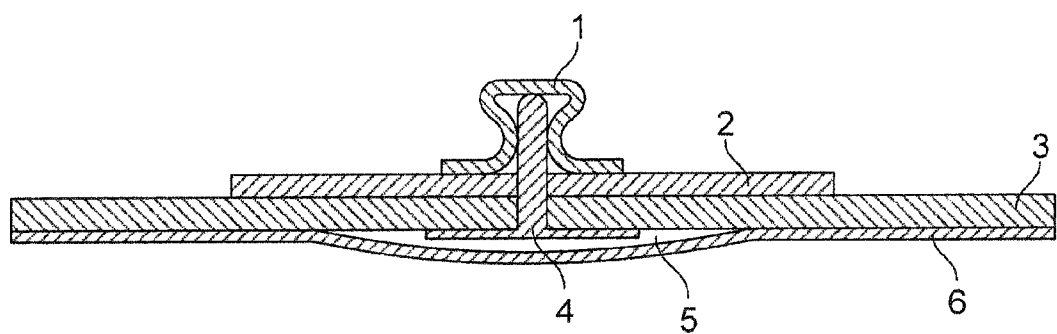

FIG. 8 is an exemplary view showing the sensor module of the present invention in an assembled state. In order to form the sensor module 10 of the present invention, the holder 17 and the amplification circuit 16 are respectively located at upper and lower portions of a space between left and right body portions 18a and 18b of the main body 18, and then the left and right body portions 18a and 18b are connected. The holder 17 and the amplification circuit 16 are latched onto stoppers 18s symmetrically formed on the left and right body portions 18a and 18b of the main body 18, and the movement of the holder 17 and the amplification circuit 16 is restrained after the left and right body portions 18a and 18b are connected. The holder 17 is integrated with the main body 18 under the condition that the upper end of the holder 17 is protruded from the upper surface of the main body 18, and is molded together with the main body 18. The holder 17 together with the cap 19 serves to fix the sensor module 10 of the present invention to a headset, and to guide the cap 19. The shape of the holder 17 is not limited. When the holder 17 is not integrated with the main body 18, the holder may be latched onto the stoppers 18s of the main body 18 and be fixedly assembled with the main body 18. The connection between the holder 17 and the main body 18, the connection between the amplification circuit 16 and the main body 18, and the connection between the holder 17 and the cap 19 are not limited to the description of the above embodiment. The above connections are apparent to those skilled in the art, and a detailed description thereof will thus be omitted.

The amplification circuit 16 is connected to the main body 18 by allowing the lower part of the spring 14 to pass a through hole 18a formed through a diaphragm 18q. When the spring 14 is initially molded, a vertical distance from one end of the spring 14 to the other end of the spring 14 is properly obtained. Thereby, when the spring 14 is compressed by the active electrode 12 inserted into the main body 18, the spring 14 has designated elastic energy. As stated in the Equation 1 below, when the spring 14 has a large constant, large force must be applied to the spring 14 for compression. Accordingly, preferably, the spring 14 has a constant determined in the proper range of deviation from 150 gf/4.5 mm.

$$k=P/a \qquad \text{Equation 1}$$

wherein k represents the constant of the spring 14, P represents load, and a represents variation.

Thereafter, the spring 14 and the amplification circuit 16 are located in the main body 18, and the cap 19 is inserted into the holder 17 fixed to the insertion hole 18h formed through the upper surface of the main body 18 under the condition that the active electrode 12 is interlocked with the cap 19. Screw threads and screw hollows, which are engaged with those of the holder 17, are formed on the cap 19. After screw threads and screw hollows formed on the cap 19 and the insertion hole 18h are engaged with each other, and the cap 19 is rotated to the end, thus being fixed. The protruded height of the active electrode 12 is adjusted by rotating the cap 19 inserted into the holder 17. Thereby, the active electrode 12 compresses the spring 14, and the spring 14 has elastic energy and semi-permanently elastically moves under the condition that the active electrode 12 is inserted into the main body 18 by interference fit. One end 14a and the other end 14b of the spring 14 respectively contact the active electrode 12 and the amplification circuit 16 so that the biomedical signal received from the active electrode 12 is transmitted to the amplification circuit 16. The active electrode 12 slides along the inner surface of the cap 19, and the sliding of the active electrode 12 is restrained by latching the latching protrusion 12a formed on the lower part of the active electrode 12 onto the lower end of the cap 19. Preferably, the active electrode 12 has a proper overall height so that the active electrode 12 is protruded outwardly from the upper surface of the cap 19 by a designated height after the active electrode 12 is completely inserted into the cap 19. Preferably, in order to improve conductance of the active electrode 12 and the spring 14, the active electrode 12 and the spring 14 are plated with gold or silver. 5

As apparent from the above description, the present invention provides an active dry sensor module for measurement of bioelectricity, which excludes the use of a conductive gel, thereby not supplying unpleasantness and discomfort to a reagent and preventing the danger of viral infection. Further, the active dry sensor module of the present invention excludes the use of a wire for transmission of a biomedical signal, thereby preventing the interference of the signal due to a noise component generated from a power source. Moreover, the active dry sensor module of the present invention amplifies the biomedical signal to a designated treatable level, thereby precisely and easily measuring the biomedical signal.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

The invention claimed is:

1. An active dry sensor module comprising:
    a hollow main body having an upper surface with an insertion hole formed through the upper surface;
    a holder fixably inserted into the insertion hole of the hollow main body, the holder including holder screw threads and screw hollows;
    a cap with a hole and a lower part with cap screw threads and screw hollows, the cap inserted into the holder and interlocking with the holder by the holder screw threads and screw hollows mating with the cap screw threads and screw hollows;

an active electrode inserted into the hole of the cap so that the active electrode is slidable relative to the cap, the active electrode having a contactable upper surface and a latching protrusion protruded from a lower part of the active electrode that is capable of being latched onto a lower end of the cap, wherein the active electrode having the contactable upper surface is slidable relative to the cap for directly contacting a portion of a scalp of a user that is using the active dry sensor module, wherein the active electrode has a cap shape that is capable of contacting a skin surface of a user, and wherein a height of the active electrode protruding from the cap is adjusted by rotating the cap inserted in the holder;

a resilient member with a first end contacting the lower part of the active electrode, installed in the main body, and electrically connected to the main body; and an amplification circuit, installed in the main body and coupled to a second end of the resilient member, that is capable of receiving and processing a biomedical signal passed through the resilient member from the active electrode.

2. The active dry sensor module as set forth in claim 1 further comprising a headset inserted between the cap and the holder so that the main body is attached to and detached from the headset.

3. The active dry sensor module as set forth in claim 1, wherein the amplification circuit further comprises:

an instrumentation amplifier for amplifying the biomedical signal with a high common mode rejection ratio and a signal pass band, wherein the instrumentation amplifier includes three amplifiers that provide a differential amplifier and two amplifiers to form a feedback loop thereby having band pass characteristics and an amplification function;

a band-pass filter for filtering the output signal from the instrumentation amplifier;

a notch filter for eliminating a noise component of 60 Hz contained in the output signal from the instrumentation amplifier;

and an amplifier.

4. The active dry sensor module as set forth in claim 1, wherein the active electrode and the resilient member are plated with gold or silver.

5. The active dry sensor module as set forth in claim 1, wherein the active electrode has a curved upper surface capable of contacting a skin surface.

6. The active dry sensor module as set forth in claim 1, wherein the active electrode has an uneven surface capable of contacting a skin surface.

7. The active dry sensor module of claim 1, wherein the resilient member further comprises a spring.

8. The active dry sensor module of claim 1, wherein the resilient member biases the active electrode against a surface of a user that is using the active dry sensor module.

* * * * *